US008642350B2

(12) United States Patent
Papkovsky

(10) Patent No.: US 8,642,350 B2
(45) Date of Patent: Feb. 4, 2014

(54) SENSOR MATERIAL AND USES THEREOF TO SIMULTANEOUSLY SENSE TWO ANALYTES: OXYGEN AND PH OR ACIDIC/BASIC GASEOUS IONS

(75) Inventor: Dmitri Papkovsky, County Cork (IE)

(73) Assignee: University College Cork, National University of Ireland, Cork, Cork (IE)

( * ) Notice: Subject to any disclaimer, the term of this patent is extended or adjusted under 35 U.S.C. 154(b) by 363 days.

(21) Appl. No.: 13/074,187

(22) Filed: Mar. 29, 2011

(65) Prior Publication Data
US 2011/0236986 A1 Sep. 29, 2011

(30) Foreign Application Priority Data

Mar. 29, 2010 (EP) .................................. 10158270

(51) Int. Cl.
  *G01N 31/22* (2006.01)
  *G01N 21/80* (2006.01)
  *G01N 21/77* (2006.01)
(52) U.S. Cl.
  USPC ..................... 436/136; 422/82.05; 422/82.06; 422/82.07; 422/82.08; 422/82.09; 436/100; 436/101; 436/102; 436/122; 436/163; 436/164; 436/166; 436/172
(58) Field of Classification Search
  USPC ............ 422/82.05–82.09; 436/100–102, 122, 436/136, 163–164, 166, 172
  See application file for complete search history.

(56) References Cited

U.S. PATENT DOCUMENTS

| | | | | |
|---|---|---|---|---|
| 4,810,655 | A * | 3/1989 | Khalil et al. .................. | 436/138 |
| 5,304,495 | A * | 4/1994 | Yim ................................ | 436/68 |
| 5,718,842 | A * | 2/1998 | Papkovsky et al. ...... | 252/301.16 |
| 5,863,460 | A * | 1/1999 | Slovacek et al. ......... | 252/301.35 |
| 6,074,607 | A * | 6/2000 | Slovacek et al. ......... | 422/82.08 |
| 6,607,300 | B1 * | 8/2003 | Kleinerman ................. | 374/120 |
| 6,840,669 | B2 * | 1/2005 | Kleinerman .................. | 374/120 |
| 2002/0098120 | A1 * | 7/2002 | Blazewicz et al. ......... | 422/82.07 |
| 2005/0037512 | A1 * | 2/2005 | Yeh et al. ...................... | 436/166 |
| 2008/0051646 | A1 | 2/2008 | Papkovsky | |

FOREIGN PATENT DOCUMENTS

EP         0477501         4/1992

OTHER PUBLICATIONS

Gewehr, P. M. et al., Medical & Biological Engineering & Computing 1993, 31, 2-10.*

(Continued)

*Primary Examiner* — Arlen Soderquist
(74) *Attorney, Agent, or Firm* — Cesari and McKenna, LLP

(57) ABSTRACT

A sensor material of the type comprising a long-decay photoluminescent, protonable dye embedded in a suitable polymeric matrix, is used for generating a specific optical response to two different analytes present in a sample, thus allowing selective determination of the two analytes in the sample. Also described is a method for the simultaneous sensing of a first and second analyte in a sample. The method comprises the steps of irradiating a sensor material of the type comprising a long-decay photoluminescent protonable dye embedded in a suitable polymeric matrix with light of one or two wavelengths, determining photoluminescence intensity and lifetime signals originating from the sensor, and correlating the photoluminescence intensity signal with a concentration of the first analyte and the photoluminescence lifetime signal(s) with the concentration of the second analyte.

14 Claims, 5 Drawing Sheets

(56) References Cited

OTHER PUBLICATIONS

Gewehr, P. M. et al., Medical & Biological Engineering & Computing 1993, 31, 11-21.*
Papkovsky, D. B. et al., Analytica Chimica Acta 1997, 337, 201-205.*
Papkovsky, D. B. et al., Spectrochimica Acta A 1997, 53m 613-621.*
Nagl, S. et al., Analyst 2007, 132, 507-511.*
Papkovsky et al. "Protonation of porphyrins in liquid PVC membranes: Effects of anionic additives and application to pH-sensing"; Journal of Photochemistry and Photology; 104:151-158 (1997).
Douglas et al. "Response characteristics of thin film oxygen sensors, Pt and Pd octaethylporphyrins in polymer films"; Sensors and Actuators B; 82(2-3):200-208 (2002).

* cited by examiner

Me=$Pt^{2+}$,$Pd^{2+}$ $Pt^{2+}$: $R_{1-8}$= $CH_3$-$CH_2$-

$Pd^{2+}$: $R_{1,3,5,7}$-$CH_3$-, $R_{2,4,6,8}$-$COOCH_3$-$CH_2$-$CH_2$-

1. Pd-OEP-CH=NMe
2. Pd-OEP-CH=NMe +TFA
3. Pt-EP-CH=NMe
4. Pt-EP-CH=NMe + TFA

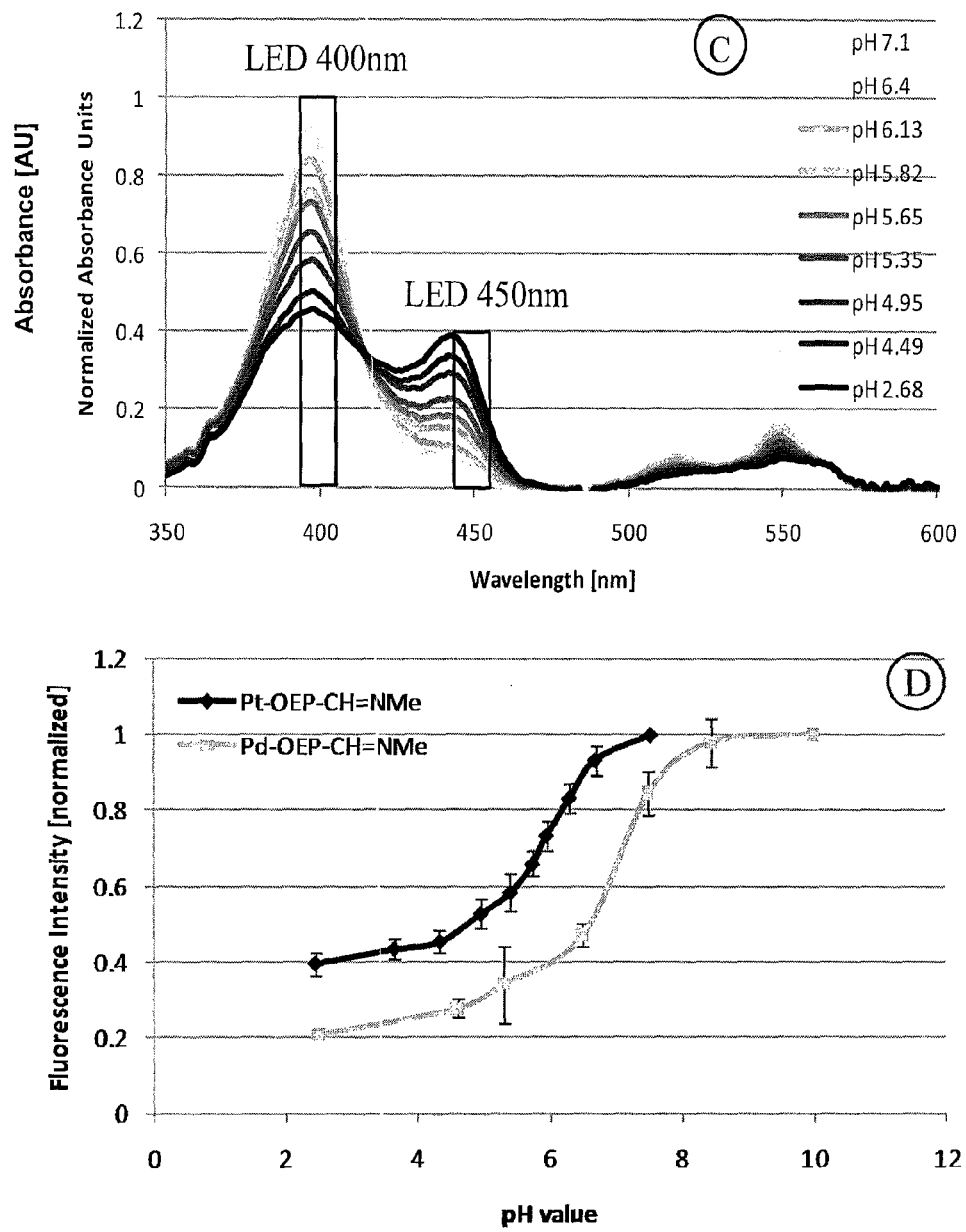
FIGURE 2 (CONTD.)

FIGURE 4 (CONTD.)
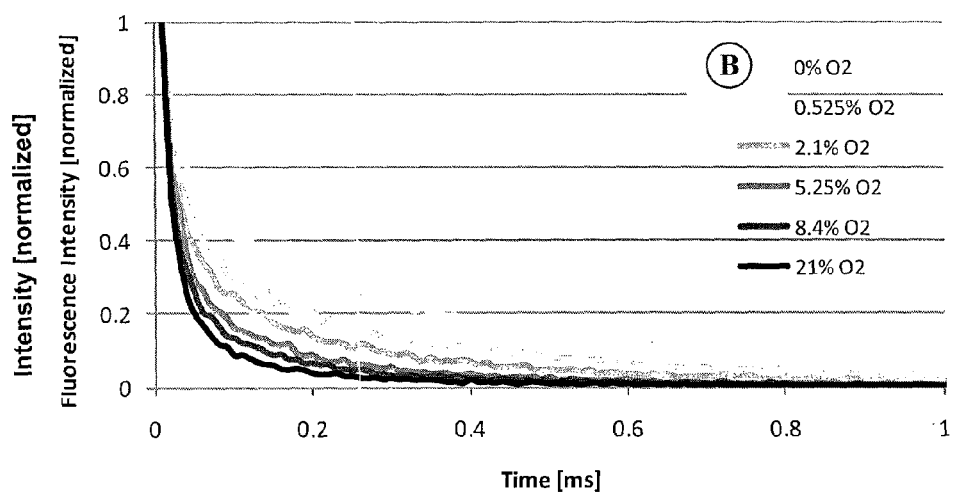

SENSOR MATERIAL AND USES THEREOF TO SIMULTANEOUSLY SENSE TWO ANALYTES: OXYGEN AND PH OR ACIDIC/BASIC GASEOUS IONS

CROSS-REFERENCE TO RELATED APPLICATIONS

This application claims the priority of European Application No. 10158270, filed on Mar. 29, 2010. The contents of the application are hereby incorporated by reference in its entirety.

INTRODUCTION

The invention relates to uses of an optically active sensor material of the type comprising a long-decay photoluminescent dye selected from phosphorescent platinum (II) and palladium (II) complexes of porphyrin dyes embedded in a polymer matrix.

BACKGROUND TO THE INVENTION

Porphyrin dyes have attractive photophysical properties, which can be exploited in optochemical sensors for the detection of a number of important analytes [1]. Their chromophoric moiety consists of an aromatic tetrapyrolic macrocycle, which can accommodate central ligand(s) such as metal ions or protons, and peripheral substituents in pyrrol and meso-positions. Modifications can also involve the macrocycle itself, giving rise to chlorins, benzoporphyrins, porphyrin-ketones, aza-porphyrins with characteristic spectral properties [2]. These features provide flexibility in tuning the optical (absorption, luminescence) and physical-chemical (hydrophilicity, linkers, additional functionality) characteristics of porphyrin dyes and in designing new reporter molecules for sensing applications.

In particular, bright, long-decay phosphorescence of Pt(II)- and Pd(II) porphyrins have allowed the development of simple and robust lifetime-based oxygen ($O_2$) sensors which are widely used nowadays and gaining popularity in many areas. Several other analytes including temperature, $SO_2$, $NO_x$ and relative humidity have been analysed by phosphorescence quenching of metalloporphyrin dyes incorporated in solid-state materials [3]. Using more complex composites and combinations of dyes, it became possible to extend the range of analytes amenable to quenched-phosphorescence sensing and to achieve multi-parametric detection [4]. However, cross-sensitivity, compromised performance, increased complexity and manufacturing costs often limit the use of such sensors. There is therefore a need for more simple and robust multi-analyte sensor systems.

Besides $O_2$, optochemical sensors for pH (as well as sensors for acidic and basic species such as $CO_2$, $SO_2$, ammonia which can be constructed on the basis of a pH transducer [5-7]) are of particular interest. pH sensors comprising protonable porphyrin dyes embedded in a placticised PVC polymer which rely on the changes in absorption and fluorescence of the porphyrin dyes have been described [12]. However the use of phosphorescence modality dual-analyte sensing approaches have not been demonstrated with such sensor systems.

SUMMARY OF THE INVENTION

Broadly, the invention relates to the use of sensor materials of the type described above [12] for use in selective determination of two distinct analytes in a sample. One of the analytes is generally molecular oxygen which is detectable due to the ability of the $O_2$ to quench phosphoresence emissions of the dye (phosphoresence lifetime). The sensor material is also capable of sensing a second analyte, for example pH (protons) or other charged moieties, for example anions and cations, due to the dye comprising a protonable moiety. The invention therefore relates to a sensor material comprising a long-decay photoluminescent, protonable dye typically embedded in a suitable polymeric matrix for use in the simultaneous determination (or dual sensing) of two analytes in a sample, wherein one of the analytes is molecular oxygen and the second analyte is a charged ion which is capable of interacting with the protonable moiety on the dye.

According to the invention, there is provided a sensor material of the type comprising a long-decay photoluminescent, protonable dye embedded in a suitable polymeric matrix, for use in generating a specific optical response to two different analytes present in a sample, thus allowing selective determination of the two analytes in the sample.

The invention also provides a method for the simultaneous sensing and/or determination of a first and second analyte in a sample comprising the steps of irradiating a sensor material of the type comprising a long-decay photoluminescent, protonable dye embedded in a suitable polymeric matrix with light of one or two wavelengths, determining photoluminescence intensity and lifetime signals originating from the sensor, and correlating the photoluminescence intensity signal with a concentration of the first analyte and the photoluminescence lifetime signal(s) with the concentration of the second analyte. Typically, the first analyte is pH ($H^+/OH^-$) or acidic/basic gaseous ions, and the second analyte is molecular oxygen.

The term "optically active" should be understood to mean characteristic optical properties (of the material) which are modulated by the analyte of interest and which can be measured with a suitable optical detector device.

The term "long decay" should be understood to mean fluorescence or phosphorescence in the microsecond time domain.

The term "protonable" should be understood to mean accepting or donating a proton (or alternatively a hydroxyl ion) by a chemical structure. In our case, this process is usually associated with changes in optical properties of the chemical structure.

In one embodiment, the sensor material is used for simultaneously sensing of molecular oxygen and pH($H^+/OH^-$). In another embodiment, the sensor material is used for simultaneously sensing of molecular oxygen and acidic/basic gases.

In this specification, the term "long-decay photoluminescent, protonable dye" generally means a phosphorescent platinum (II) and palladium (II) porphyrin dye substituted with a pH-responsive moiety, suitably proximal to the tetrapyrollic macrocycle. In a preferred embodiment of the invention, the pH-responsive moiety is a Schiff base at one meso-position on the tetrapyrollic macrocycle. In a preferred embodiment of the invention, the Schiff base has a structure —CH=N—CH$_3$, although alternative Schiff bases may be employed, the details of which will be known to those skilled in the art. In a preferred embodiment of the invention, the platinum (II) and palladium (II) complexes of porphyrin dyes are selected from the group consisting of: octaethylporphine; coproporphyrin tetramethyl ester; and octaethylporphine-ketone.

In a particularly preferred embodiment of the invention, the term "long-decay photoluminescent, protonable dye" refers to a phosphorescent dye having the following general formula:

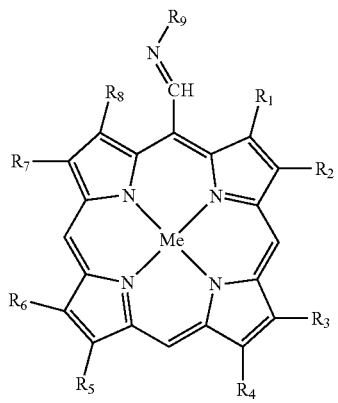

in which:
Me=$Pt^{2+}$ or $Pd^{2+}$;
$R_1$-$R_8$ are each, independently, selected from the group —$CH_3$, —$C_2H_5$, —$CH_2$—$CH_2$—CO—$R_{10}$ or $CH_2$—CO—$R_{11}$;
$R_9$ is selected from a group represented by $CH_3$, $C_2H_5$, $C_3H_7$; and
$R_{10}$, $R_{11}$ are selected from a group represented by $OCH_3$, $OC_2H_5$, $OC_3H_7$, OH, $NH_2$, NH—X, in which X is an aliphatic radical.

Suitably, X is CH=N—$R_9$, wherein $R_9$ is ideally elected from $CH_3$, $C_2H_5$, and $C_3H_7$.

In a preferred embodiment of the invention, the long-decay photoluminescent, protonable dye is selected from Pt-octaethylporphine and Pd-coproporphyrin-1-tetramethylester and is derivatised at one meso-position with a Schiff base.

Suitably, the sensor material is capable of quantitatively detecting molecular oxygen in the 0 to 10, preferably 0 to 21 KPa range (0-250 μM)

Preferably, the sensor material is capable of detecting pH in the 5-7, preferably 5-9, more preferably 3-8, and ideally 3-9 range.

The term "polymeric matrix" means a polymer, typically a plasticised PVC with an ion-transfer reagent as an additive. The plasticizer may be any suitable plasticizer capable of providing flexibility and durability to the polymer. Many examples of plasticizers will be known to the skilled person, which generally comprise phthalates or esters of polycarboxylic acids with linear or branched aliphatic alcohols of medium chain length. One particularly suitable plasticizer is bis(2-ethylhexyl)sebacate. The ion transfer reagent is generally a cation transfer reagent which consists of a small size cation and a relatively large size and hydrophobic anion. In a preferred embodiment, the ion transfer reagent is potassium tetrakis(4-chlorophenyl)borate.

Preferably, the sensor material comprises 0.01-10 mM, 0.1-1 mM, 0.2-0.5 mM, and ideally 0.2-0.3 mM photoluminscent protonable dye.

Preferably, the sensor material comprises 1-10%, typically 1-2%, ideally 1.5-2% polymer (w/v).

Preferably, the sensor material comprises 1-10%, typically 1-5%, ideally 3-4% plasticiser (w/v).

Preferably, the sensor material comprises 0.1 to 10 mM, typically 0.5-5 mM, preferably 1-5 mM, and ideally 2-3 mM ion transfer reagent.

In another embodiment of the invention, the polymeric matrix comprises an ionomer. An ionomer is a polymer that comprises repeat units of both electrically neutral repeating units and a fraction of ionized units (usually no more than 15 percent). Examples of ionomers are provided in Eisenberg, A. and Kim, J.-S., Introduction to Ionomers, New York: Wiley, 1998. Typically, this type of sensor material is provided in the form of a suspension of ionomer nanoparticles impregnated with the photoluminescent protonable dye. Preferably, the polymeric matrix comprises a suspension of Nafion® nanoparticles.

The invention also provides a sensor material comprising a long-decay photoluminescent, protonable dye embedded in a suitable polymeric matrix, in which the dye is a photoluminscent dye selected from phosphorescent platinum (II) and palladium (II) complexes of porphyrin dyes, wherein the dye is substituted with a Schiff base at one or more meso-position, for use in the detection, ideally simultaneous detection, of two analytes in a sample, in which one of the analytes is suitably molecular oxygen and the other analyte is capable of interacting with the Schiff base to cause a detectable change in the absorption spectra of the dye.

The invention also provides a sensor material comprising a long-decay photoluminescent, protonable dye embedded in a suitable polymeric matrix, in which the dye is a photoluminscent dye selected from phosphorescent platinum (II) and palladium (II) complexes of porphyrins substituted with a Schiff base at one meso-position, and wherein the polymeric matrix comprises PVC, a plasticiser, and an ion-transfer reagent, for use in the detection, ideally simultaneous detection, of two analytes in a sample, in which one of the analytes is suitably molecular oxygen and the other analyte is capable of interacting with the Schiff base to cause a detectable change in the absorption spectra of the dye.

The invention also provides a sensor material comprising a long-decay photoluminescent, protonable dye embedded in a suitable polymeric matrix, in which the dye is selected from Pt-octaethylporphyrine and Pd-coproporphyrin-1-tetramethylester, wherein the dye is substituted with a Schiff base at one or more meso-position, and wherein the polymeric matrix comprises PVC, a plasticiser, and an ion-transfer reagent, for use in the detection, ideally simultaneous detection, of two analytes in a sample, in which one of the analytes is suitably molecular oxygen and the other analyte is capable of interacting with the Schiff base to cause a detectable change in the absorption spectra of the dye.

The invention also provides a sensor material (as described above) for use in the dual sensing of pH and molecular oxygen, in which sensor material responds to molecular oxygen by changing its phosphorescence characteristics and responds to pH by changing its absorption characteristics. which allows quantification of molecular oxygen by phosphorescence lifetime measurements and quantification of pH by phosphorescence intensity measurements.

The invention also provides a sensor material (as described above) for use in the dual sensing of pH and molecular oxygen and which allows quantification of molecular oxygen by phosphorescence lifetime measurements and quantification of pH by ratiometric absorbance or reflectance measurements.

A dual pH and molecular oxygen sensor comprising a sensor material of the invention, which allows self-referencing and calibration-free sensing.

A dual pH and molecular oxygen sensor comprising a sensor material of the invention, which shows minimal cross-sensitivity between the two analytes.

The invention also provides a dual molecular oxygen and acidic/basic gas sensor comprising a sensor material of the type comprising a long-decay photoluminescent, protonable dye embedded in a suitable polymeric matrix which is additionally made impermeable to protons but permeable to acidic or basic gaseous ions thus allowing the independent determination of molecular oxygen and acidic or basic gaseous ions. Suitably, the polymeric matrix is permeable to $CO_2$, $SO_3$, $NH_3$ or amines. An example of such a sensor includes a pH-sensor of the invention coated with a layer of silicone.

The invention also relates to a sensor material of the type comprising a long-decay photoluminescent, protonable dye embedded in a suitable polymeric matrix, in which the matrix is impermeable to protons but permeable to acidic or basic gaseous ions, for use in the dual sensing of molecular oxygen and acidic/basic gaseous ions.

The invention also provides a method for the simultaneous sensing of a first and second analyte in a sample comprising the steps of irradiating a sensor material of the type comprising a long-decay photoluminescent, protonable dye embedded in a suitable polymeric matrix with light of one or two wavelengths, determining photoluminescence intensity and lifetime signals originating from the sensor, and correlating the photoluminescence intensity signal with a concentration of the first analyte and the photoluminescence lifetime signal(s) with the concentration of the second analyte. Typically, the first analyte is pH ($H^+/OH^-$) or acidic/basic gaseous ions, and the second analyte is molecular oxygen.

The invention also provides a method for the simultaneous sensing of a first and second analyte in a sample comprising the steps of:
a. irradiating a sensor material of the invention with light of one wavelength which corresponds to its absorption and excitation optimum;
b. measuring the optical signal emitted by the sensor material at a different wavelength which corresponds to sensor photoluminescence;
c. determining the photoluminescence intensity and lifetime signals originating from the sensor;
d. correlating the lifetime signal with the concentration of the first analyte;
e. correlating the lifetime signal with the contribution of the first analyte to the photoluminescence intensity from the sensor;
f. determining the residual photoluminescence intensity signal which corresponds to the second analyte; and
g. correlating the residual photoluminescence with the concentration of the second analyte.

The invention also provides a method for the simultaneous and quantitative sensing of a first and second analyte is a sample, which method comprises the steps of:
a. irradiating a sensor material of the invention with light of one wavelength which corresponds to the absorption optimum of the non-protonated form of the dye and phosphorescence excitation optimum;
b. measuring an intensity of reflected or transmitted light at this irradiation wavelength;
c. measuring at a different wavelength a photoluminescent signal from the sensor which corresponds to its emission optimum and determining its lifetime or related parameter;
d. correlating the lifetime signal with the concentration of the first analyte;
e. irradiating the sensor with light of the other wavelength which corresponds to the absorption optimum of the protonated form of the dye;
f. measuring the intensity of reflected or transmitted light at this wavelength; and
g. correlating the two reflected/transmitted light signals with the concentration of the second analyte.

Suitably, luminescence lifetime is measured indirectly by measuring a related parameter, such as luminescence phase shift, anisotropy, or intensity ratio.

Ideally, the first analyte is molecular oxygen and the second analyte is pH($H^+/OH^-$).

Typically, the lifetime signal is correlated with first analyte concentration using a pre-determined calibration function for the first analyte.

Suitably, the residual photoluminescence intensity is correlated with second analyte concentration using a pre-determined calibration function for the second analyte.

Generally, the two reflected/transmitted light signals are correlated with the second analyte concentration using a pre-determined calibration function.

The invention also relates to a sensor material of the invention for use in the simultaneous sensing of two analytes in a single sample. Generally, the sensing is quantitative determination of the two analytes. Typically, one of the analytes is molecular oxygen, in which the sensor material is employed to quantitatively detect molecular oxygen in a range of 0-10 KPa, and ideally 0–21 kPa (0-250 mM). Suitably, one of the analytes is pH($H^+/OH^-$), in which the sensor material is employed to quantitatively detect pH in a range of 5-7, 5-8, 3-7, 3-8, and ideally 3-9 pH units.

Thus, in a preferred embodiment of the invention, the invention provides a sensor material of the invention for use in quantitative (and ideally simultaneous) detection sensing of molecular oxygen in the 0-10 KPa, and ideally 0-21 KPa, range and pH in the 5-7, and ideally 5-8 range.

The invention also relates to a system for the simultaneous sensing of a first and second analyte in a sample comprising:
a sensor material of the type comprising a long-decay photoluminescent protonable dye embedded in a suitable polymeric matrix, in which the dye typically is a photoluminscent dye selected from the group represented by phosphorescent platinum (II) and palladium (II) porphyrins substituted at one meso-position with a protonable group;
means for irradiating the sensor material with light of one, and ideally at least two, wavelengths;
means for measuring a photoluminescence lifetime signal of light originating from the sensor material;
means for measuring a photoluminescence intensity signal of light originating from the sensor material; and
optionally, processing means for correlating the photoluminescence lifetime signal with a concentration of the second analyte and/or for correlating the photoluminescence intensity signal(s) with a concentration of the first analyte.

CH$_3$ (♦) and Pd-OEP-CH=N—CH$_3$ (■) at 24° C. and 30° C. respectively (emission intensity) (D), measured in sodium acetate.

Figure 3:
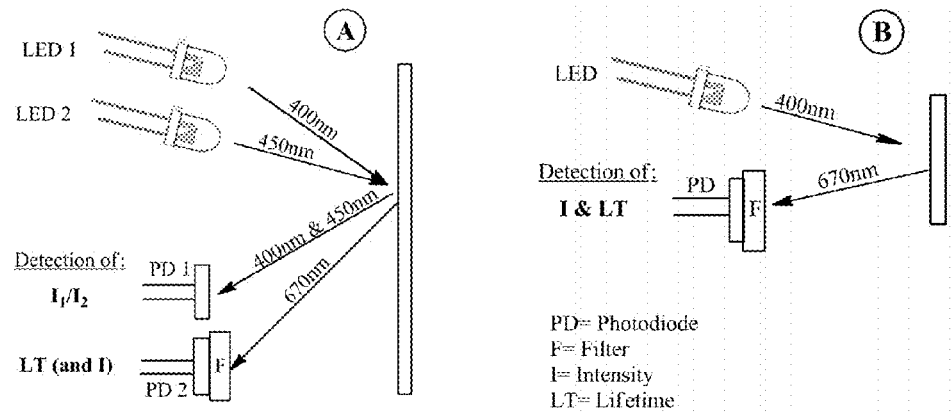

FIG. 3: Two different sensing schemes. (A) Absorbance or transmission measurements conducted at two wavelengths (2 LEDs) which can be used to construct a simple detection system which implements ratiometric absorbance based sensing pH and phosphorescence lifetime based sensing of dissolved O$_2$. (B) Quantification and continuous monitoring of the two analytes can be achieved by measuring the phosphorescence intensity (O$_2$, pH) and lifetime (O$_2$).

Figure 4:
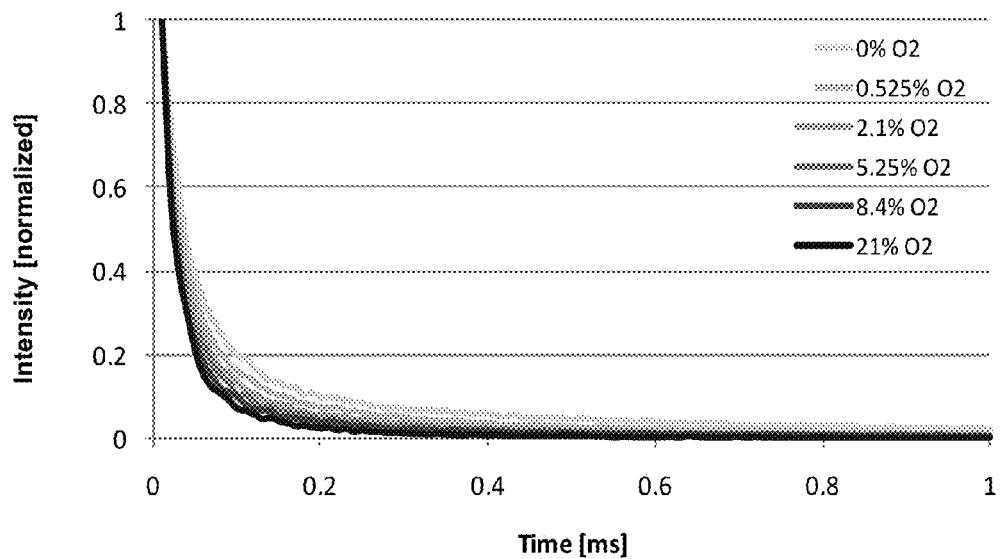

FIG. 4: Decay curves of A) Pt-OEP-CH=N—CH$_3$, B) Pd-OEP-CH=N—CH$_3$.

DETAILED DESCRIPTION OF THE INVENTION

Figure 1:
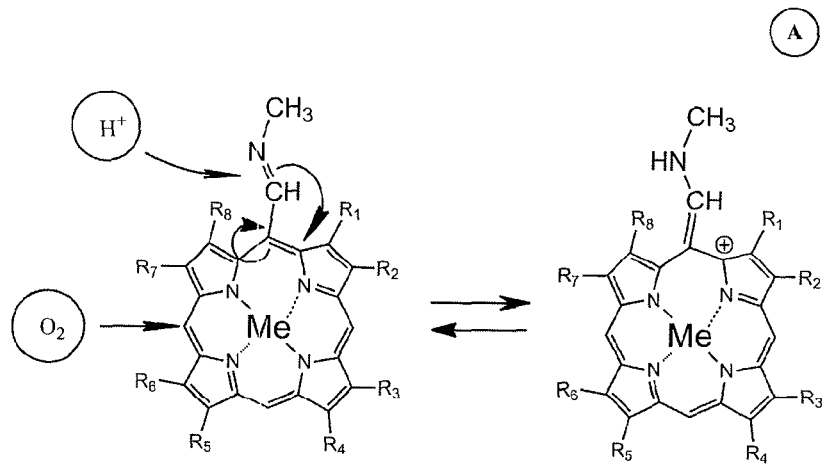
FIG. 1: General chemical structures of the dyes and interaction sites for $H^+$ and $O_2$ (A) and changes in absorption spectra upon protonation (B).
Figure 1:
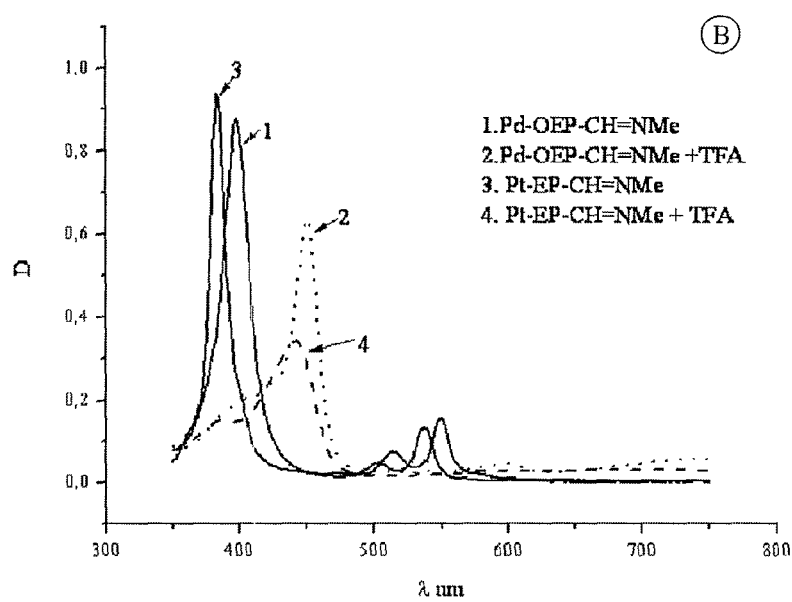

A new group of solid-state materials based on a single phosphorescent reporter dye, which in one embodiment allow simultaneous, reversible sensing of both dissolved O$_2$ and pH, are described. The reporter preferably comprises the derivative of hydrophobic Pt-octaethylporphyrine (PtOEP-CH=N—CH$_3$) or Pd-coproporphyrin-I tetramethylester (PdCPE-CH=N—CH$_3$) dyes which contain a pH-responsive moiety proximal to the tetrapyrrolic macrocyle (for example, substitution at one meso-position with a Schiff-base group—see FIG. 1A). In the unprotonated state such a dye displays normal metalloporphyrin-type of electronic spectra with the characteristic Soret and visible absorbance bands and bright room temperature phosphorescence in the red region. This form of the dye displays bright phosphorescence at room temperature which is susceptible to dynamic quenching by molecular oxygen. Thus, O$_2$ reduces phosphorescence intensity and lifetime of the dye. Like for normal porphyrins, the spectra for the Pd-complex are slightly red-shifted compared to Pt-complex (see FIG. 1B) and lifetime is several times longer (see Table 1).

On the other hand, protonation of the peripheral group (Schiff base) leads to the formation of a delocalised carbocation represented by 10 resonant structures [3]. This process is accompanied by major spectral changes: a shift in absorbance peak from 398 nm to 443 nm and the disappearance of the porphyrin type of electronic spectra and phosphorescence. The process is reversible and potentially allows for sensing of the protonation or pH changes by means of absorbance or phosphorescence measurements.

Preparation of the Sensors:

A typical of our sensors was prepared as follows. High molecular weight PVC (120 mg) and bis(2-ethylhexyl)sebacate (240 mg) are dissolved in 3 g of Tetrahydrofuran. Pt-OEP-CH=N—CH$_3$ dye is dissolved in chloroform (10 mM stock) and potassium tetrakis(4-chlorophenyl)borate—in THF (10 mM stock). The final sensor formulation which was found to be optimal is shown in Table 1.

TABLE 1

Sensor composition after drying of optimal solid state sensors (Pd, Pt)

|  | Pt-OEP-CH=N—CH$_3$ [%] | Pd-OEP-CH=N—CH$_3$ [%] |
|---|---|---|
| dye | 0.35 | 0.16 |
| additive | 2.3 | 3.92 |
| plasticizer | 3.5 | 3.5 |
| PVC | 1.75 | 1.75 |
| Solvent | 92 | 91 |

This cocktail of sensor components was applied in 2 μl aliquots on a solid support (e.g. Mylar® foil or microporous polymeric membrane) and left to evaporate all the solvents. This resulted in the formation of phosphorescent thin film coatings (~5 micron thick) which can be used as optochemical sensors. Other sensor formulations can also be used, such formulations are known to specialists in the area.

Thin film (~5 μm) sensor coatings produced according to Table 1 were studied for their photophysical, O$_2$ and pH sensing properties. The two dyes showed similar spectral characteristics (absorption and emission), however their sensitivity to O$_2$ and pH was quite different. The main characteristics of the dual-analyte sensors based on Pt-OEP-CH=N—CH$_3$ and Pd—CPE-CH=N—CH$_3$ dyes are summarised in Table 2.

TABLE 2

Characteristics of Pt—OEP—CH=NMe and Pd—OEP—CH=NMe in solid state sensor form

| | Absorption [nm] | Emission [nm] | pK$_a$ value (21% O$_2$) 0 mM NaCl | pK$_a$ value (21% O$_2$) 500 mM NaCl | Lifetime [μs] 0% O$_2$ | Lifetime [μs] 21% O$_2$ |
|---|---|---|---|---|---|---|
| Pt—OEP—CH=NMe | 398 (pH 8.0) 443 (pH 2.0) | 670 | 4.3 (24° C.) 5.9 (30° C.) | 5.5 (30° C.) | 60 (24° C.) | 36 (24° C.) |
| Pd—CPE—CH=NMe | 398 (pH 8.0) 443 (pH 2.0) | 673 | 5.9 (24° C.) 6.9 (30° C.) | 5.5 (24° C.) 6.5 (30° C.) | 172 (24° C.) | 33 (24° C.) |

Figure 2:
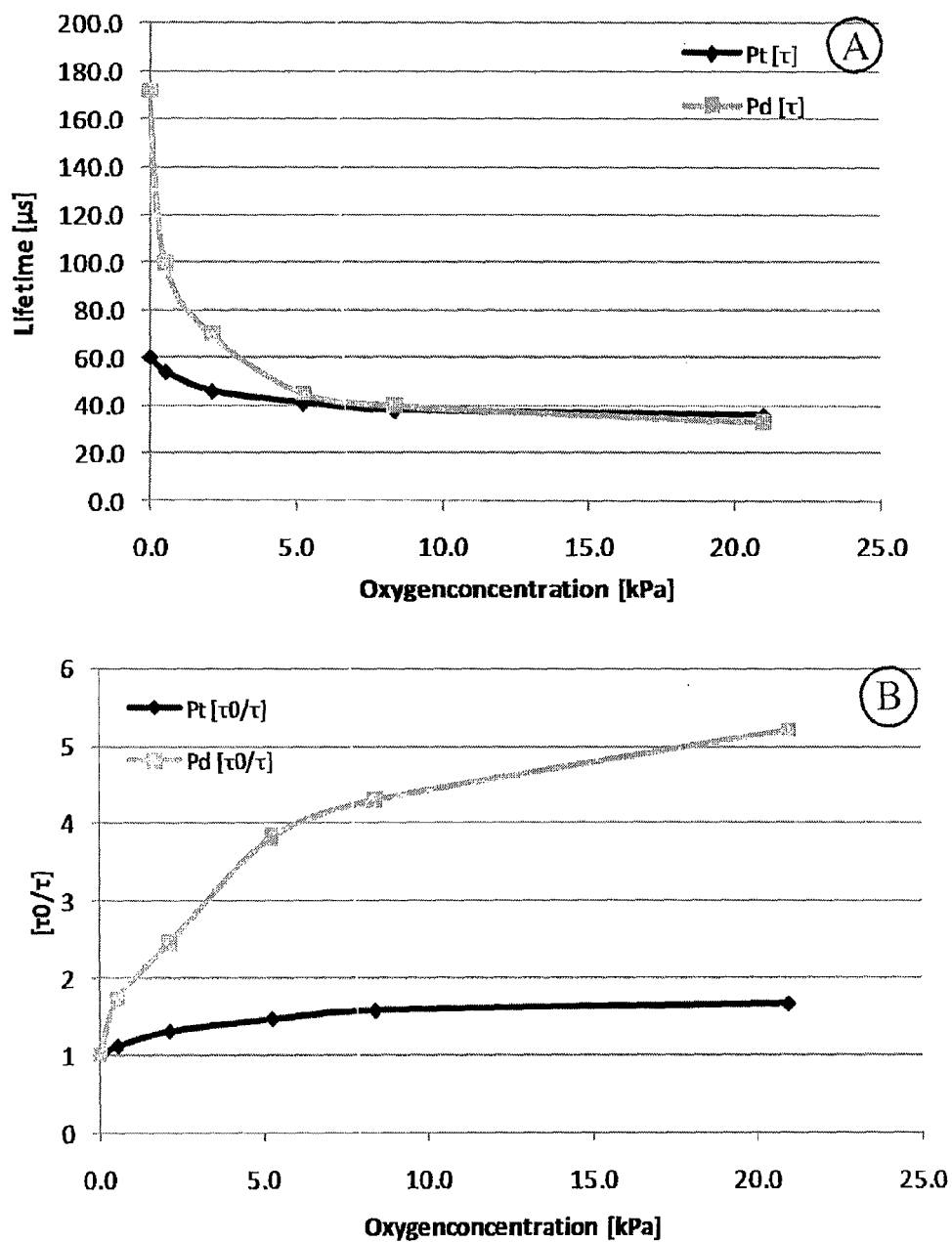
FIG. 2: Oxygen calibration in the phosphorescence lifetime (A) and Stern-Volmer (right) scales for the Pt-OEP-CH=N—$CH_3$ (♦) and Pd-OEP-CH=N—$CH_3$ (■) sensors, measured in sodium acetate, pH 6 at 24° C. (B). pH calibration of Pt-OEP-CH=N—$CH_3$ (absorbance) at certain pH steps, the two black bars show the bandwidth of commercial LEDs at 400 nm and 450 nm (C) and of Pt-OEP-CH=N—

In particular, when placed in aqueous solutions the Pt-OEP-CH=N—CH$_3$ sensors showed a moderate quenching by dissolved O$_2$. The unquenched phosphorescence lifetime of 70 μs in O$_2$-free buffer (at 24° C.) was close to that of the other Pt-porphyrins and O$_2$ sensors on their basis [3, 13]. In air-saturated solution (20.9 kPa or 250 μM) the lifetime was reduced by approximately 60%. The Pd-OEP-CH=N—CH$_3$ sensor which had the unquenched lifetime of 147 ms (several fold longer than Pt-porphyrins though slightly lower than Pd-porphyrins) showed a more favorable quenchability and changes in phosphorescence lifetime within the physiological range of 0–21 kPa O$_2$. Full O$_2$ calibrations of the two sensors show a pronounced non-linearity of Stern-Volmer plots (in FIG. 2B).

With respect to their pH sensitivity, the two sensors produced the anticipated spectral responses which occurred in the useful range of pH. Absorption spectra showed characteristic changes being similar for the two dyes (Table and FIG. 2C). Along with the changes in absorption spectra, a marked decrease in the phosphorescence intensity was observed at low pH values (when measured in air-saturated buffer solution at 24° C.). However, the decrease in phosphorescence intensity signal occurred without any significant changes in the phosphorescence lifetime. Interestingly, the Pt-OEP-CH=N—CH$_3$ sensor showed a significantly more acidic pK$_a$ (by ~1 pH unit) than the Pd-OEP-CH=N—CH$_3$ sensor, with the latter covering the important physiological range 6.5-8.0, and the former—the range 5-7.

The dual-analyte sensor based on Pd-OEP-CH=N—CH$_3$ dye is well suited for the sensing of pH and O$_2$ within the physiological ranges (pH 6-8 and 0-200 μM O$_2$, respectively). From the data presented it is also clear that the response of the O$_2$ sensor, if measured in the phosphorescence lifetime modality, is independent on the protonation process. In other words, it shows no cross-sensitivity to pH which only affects the phosphorescence intensity signal. Furthermore, sensing of pH with this dual sensor can be conducted by absorbance or transmission measurements at two wavelengths (see FIG. 3A), so that signal readout is not affected by the second analyte (O$_2$ does not cause any spectral changes) and also incorporates the internal referencing (ratiometric scheme). In this case, the whole system becomes essentially independent on a number of principle variables, such as dye concentration, optical properties of the sample, geometrical alignment, photobleaching, which makes it stable, robust and simple at the same time. It is worth noting that absorbance maxima of the neutral and protonated forms of the dye match the emission bands of the two common LEDs (400 nm and 450 nm, respectively; http://www.roithner-laser.com). These LEDs (having bandwidth of <20 nm) can be used to construct a simple detection system which implements ratiometric absorbance based sensing pH and phosphorescence lifetime based sensing of dissolved O$_2$. Alternatively, quantification and continuous monitoring of the two analytes can be achieved by measuring the phosphorescence intensity (O$_2$, pH) and lifetime (O$_2$) signals from the dual-sensors, and correcting the total intensity signal for the contribution of O$_2$ sensor (see FIG. 3B). However, such sensing scheme, although uses a more simple optical schematics, requires pH calibration and/or fixed measurement geometry.

The present Application describes a dual-analyte optochemical sensor for dissolved O$_2$ and pH, which employs just one reporter dye (for example meso-substituted Pd- or Pt-porphyrin Schiff base) embedded in a polymer matrix (for example, a plasticized PVC membrane). The new sensor chemistry allows simple internal-referencing schemes for the two analytes (for example, phosphorescence lifetime based sensing for O$_2$ and ratiometric absorbance/transmission sensing for pH). The dual-sensing approach is applicable to include other analytes, for example sensors for acidic gases (CO$_2$, SO$_2$) designed on the basis of pH transducer, enzyme biosensors.

The invention is not limited to the embodiments hereinbefore described which may be varied in construction and detail without departing from the spirit of the invention.

References
1. Wolfbeis, O. S., *Fiber-Optic Chemical Sensors and Biosensors*. Analytical Chemistry, 2008. 80 (12): p. 4269-4283.
2. Dolphin, D., *The porphyrins. vol. 3. part. A; physical chemistry.* 1978: Academic Pr.
3. Papkovsky, D. B. and T. C. O'Riordan, *Emerging applications of phosphorescent metalloporphyrins*. Journal of Fluorescence, 2005. 15 (4): p. 569-584.
4. Nagl, S. and O. Wolfbeis, *Optical multiple chemical sensing: status and current challenges*. The Analyst, 2007. 132 (6): p. 507-511.
5. Borisov, S. M., et al., *Optical Carbon Dioxide Sensors Based on Silicone-Encapsulated Room-Temperature Ionic Liquids*. Chemistry of Materials, 2007. 19 (25): p. 6187-6194.
6. Wolfbeis, O. and A. Sharma, *Fibre-optic fluorosensor for sulphur dioxide*. Analytica Chimica Acta, 1988. 208: p. 53-58.
7. Kukla, A., Y. Shirshov, and S. Piletsky, *Ammonia sensors based on sensitive polyaniline films*. Sensors & Actuators: B. Chemical, 1996. 37 (3): p. 135-140.
8. Borisov, S. M., et al., *Precipitation as a simple and versatile method for preparation of optical nanochemosensors*. Talanta, 2009. 79 (5): p. 1322-1330.
9. Wolfbeis, O. S., *Materials for fluorescence-based optical chemical sensors*. Journal of Materials Chemistry, 2005. 15: p. 2657-2669.
10. Apostolidis, A., et al., *A combinatorial approach for development of materials for optical sensing of gases*. J. Comb. Chem., 2004. 6 (3): p. 325-331.
11. Hartmann, P. and W. Trettnak, *Effects of polymer matrices on calibration functions of luminescent oxygen sensors based on porphyrin ketone complexes*. Analytical chemistry (Washington, D.C.), 1996. 68 (15): p. 2615-2620.
12. Papkovsky, D. B., G. V. Ponomarev, and O. S. Wolfbeis, *Protonation of porphyrins in liquid PVC membranes: Effects of anionic additives and application to pH-sensing*. Journal of Photochemistry and Photobiology a-Chemistry, 1997. 104 (1-3): p. 151-158.
13. Douglas, P. and K. Eaton, *Response characteristics of thin film oxygen sensors, Pt and Pd octaethylporphyrins in polymer films*. Sensors & Actuators: B. Chemical, 2002. 82 (2-3): p. 200-208.

The invention claimed is:
1. A method for the simultaneous quantitative sensing/determination of two analytes in a sample, in which a first analyte is oxygen and a second analyte is selected from pH (H$^+$ or OH$^-$) and acidic/basic gaseous ions, which method comprises the steps of:
irradiating a sensor material with light of one or two wavelengths,
determining photoluminescence lifetime and intensity signals originating from the sensor, and
correlating the photoluminescence intensity signal with a concentration of the oxygen in the sample and the photoluminescence lifetime signal with the pH or the concentration of the acidic/basic gaseous ions,
wherein the sensor comprises a long decay photoluminescent protonable dye embedded in a polymer, in which the dye in a phosphorent platinum (II) or palladium(II) porphyrin dye is substituted with a pH-responsive Schiff base.

2. A method as claimed in claim 1 in which the dye is a phosphorescent dye having the following general formula:

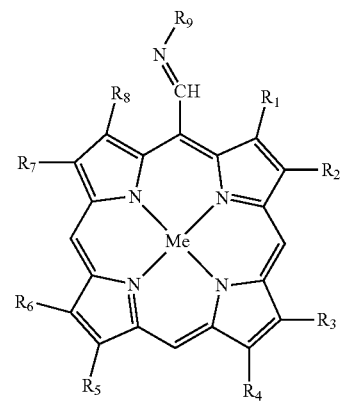

in which:

Me=Pt$^{2+}$ or Pd$^{2+}$;

$R_1$-$R_8$ are each, independently, selected from the group—CH$_3$, —C$_2$H$_5$, —CH$_2$—CH$_2$—CO—R$_{10}$ or CH$_2$—CO—R$_{11}$;

$R_9$ is selected from a group represented by CH$_3$, C$_2$H$_5$, C$_3$H$_7$; and $R_{10}$, $R_{11}$ are selected from a group represented by OCH$_3$, OC$_2$H$_5$, OC$_3$H$_7$, OH, NH$_2$, NH—X, in which X is an aliphatic radical.

3. A method as claimed in claim 1 and comprising the steps of:
   a. irradiating a sensor material of the type comprising a long-decay photoluminescent protonable dye embedded in a suitable polymeric matrix with light of one wavelength which corresponds to its absorption and excitation optimum;
   b. measuring the optical signal emitted by the sensor material at a different wavelength which corresponds to sensor photoluminescence;
   c. determining the photoluminescence intensity and lifetime signals originating from the sensor;
   d. correlating the lifetime signal with the concentration of the first analyte;
   e. correlating the lifetime signal with the contribution of the first analyte to the photoluminescence intensity from the sensor;
   f. determining the residual photoluminescence intensity signal which corresponds to the second analyte; and
   g. correlating the residual photoluminescence with the concentration of the second analyte.

4. A method as claimed in claim 1, which method comprises the steps of:
   h. irradiating a sensor material of the type comprising a long-decay photoluminescent protonable dye embedded in a suitable polymeric matrix with light of one wavelength which corresponds to the absorption optimum of the non-protonated form of the dye and photoluminescence excitation optimum;
   i. measuring an intensity of reflected or transmitted light at this irradiation wavelength;
   j. measuring at a different wavelength a photoluminescent signal from the sensor material which corresponds to its emission optimum and determining its lifetime or related parameter;
   k. correlating the photoluminescence lifetime signal with the concentration of the first analyte;
   l. irradiating the sensor material with light of the other wavelength which corresponds to the absorption optimum of the protonated form of the dye;
   m. measuring the intensity of reflected or transmitted light at this wavelength; and
   n. correlating the two reflected/transmitted light signals with the concentration of the second analyte.

5. A method as claimed in claim 1 in which the phosphorent porphyrin dye is selected from Pt-octaethylporphyrine and Pd-coproporphyrin-1-tetramethylester.

6. A method as claimed in claim 1 in which the polymeric matrix comprises PVC, a plasticiser, and an ion-transfer reagent.

7. A method as claimed in claim 6 in which the plasticizer is selected from the group consisting of: bis(2-ethylhexyl) sebacate nitrophenyloctylether and cyanophenyloctylether.

8. A method as claimed in claim 6 in which the ion transfer reagent is selected from the group consisting of: potassium tetrakis(4-chlorophenyl)borate, potassium tetrakis(4-biphenylyl)borate, and ammonium tetrakis(4-chlorophenyl)borate.

9. A method as claimed in any of claim 1 in which the polymer comprises a suspension of polymeric nanoparticles, in which the dye is impregnated into the polymeric nanoparticles.

10. A method as claimed in claim 1 in which the dye in a phosphorent platinum (II) or palladium(II) porphyrin dye substituted with a pH-responsive Schiff base at the one meso position of the porphyrin dye.

11. A method as claimed in claim 1 which is capable of quantitatively detecting molecular oxygen in the 0 to 10, preferably 0 to 21 KPa range.

12. A method as claimed in claim 1 which is capable of detecting pH in the 5-7, preferably 3-7, and ideally 3-8 range.

13. A system for the simultaneous quantitative sensing/determination of two analytes in a sample, in which a first analyte is oxygen and a second analyte is selected from pH(H$^+$ or OH$^-$) and acidic/basic gaseous ions, the system comprising:
   a sensor comprising a long decay photoluminescent protonable dye embedded in a polymer, in which the dye in a phosphorent platinum (II) or palladium(II) porphyrin dye substituted with a pH-responsive Schiff base;
   means for irradiating the sensor material with light of one wavelength which corresponds to its absorption and excitation optimum;
   means for measuring the optical signal emitted by the sensor material at a different wavelength which corresponds to sensor photoluminescence;
   means for determining the photoluminescence intensity and lifetime signals originating from the sensor;
   means for correlating the lifetime signal with the concentration of the first analyte;
   means for correlating the lifetime signal with the contribution of the first analyte to the photoluminescence intensity from the sensor;
   means for determining the residual photoluminescence intensity signal which corresponds to the second analyte; and
   means for correlating the residual photoluminescence with the concentration of the second analyte.

14. A system for the simultaneous quantitative sensing/determination of two analytes in a sample, in which a first analyte is oxygen and a second analyte is selected from pH(H$^+$ or OH$^-$) and acidic/basic gaseous ions, the system comprising:
   a sensor comprising a long decay photoluminescent protonable dye embedded in a polymer, in which the dye in a phosphorent platinum (II) or palladium(II) porphyrin dye substituted with a pH-responsive Schiff base;
   means for irradiating a sensor material of the type comprising a long-decay photoluminescent protonable dye embedded in a suitable polymeric matrix with light of one wavelength which corresponds to the absorption optimum of the non-protonated form of the dye and photoluminescence excitation optimum;
   means for measuring an intensity of reflected or transmitted light at this irradiation wavelength;
   means for measuring at a different wavelength a photoluminescent signal from the sensor material which corresponds to its emission optimum and determining its lifetime or related parameter;
   means for correlating the photoluminescence lifetime signal with the concentration of the first analyte;

means for irradiating the sensor material with light of the other wavelength which corresponds to the absorption optimum of the protonated form of the dye;
means for measuring the intensity of reflected or transmitted light at this wavelength; and
means for correlating the two reflected/transmitted light signals with the concentration of the second analyte.

* * * * *

UNITED STATES PATENT AND TRADEMARK OFFICE
CERTIFICATE OF CORRECTION

PATENT NO. : 8,642,350 B2
APPLICATION NO. : 13/074187
DATED : February 4, 2014
INVENTOR(S) : Dmitri Papkovsky Page 1 of 1

It is certified that error appears in the above-identified patent and that said Letters Patent is hereby corrected as shown below:

In the Claims:

Col. 10, line 45: ~~phosphorent platinum (II) or palladium (II) porphyn dye is~~ should read <u>phosphorescent platinum (II) or palladium (II) porphyn dye</u>

Signed and Sealed this
Thirteenth Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,642,350 B2  
APPLICATION NO. : 13/074187  
DATED : February 4, 2014  
INVENTOR(S) : Dmitri Papkovsky Page 1 of 1

It is certified that error appears in the above-identified patent and that said Letters Patent is hereby corrected as shown below:

In the Claims:

Col. 10, line 44: ~~protonable dye embedded in a polymer, in which the dye in a~~ should read <u>protonable dye embedded in a polymer, in which the dye is a</u>

Col. 11, line 57: ~~A method as claimed in claim 1 in which the phosphorent~~ should read <u>A method as claimed in claim 1 in which the phosphorescent</u>

Col. 12, line 9: ~~phosphorent platinum (II) or palladium(II) porphyrin dye~~ should read <u>phosphorescent platinum (II) or palladium(II) porphyrin dye</u>

Col. 12, line 23: ~~tonable dye embedded in a polymer, in which the dye in~~ should read <u>tonable dye embedded in a polymer, in which the dye is</u>

Col. 12, line 24: ~~a phosphorent platinum (II) or palladium(II) porphyrin~~ should read <u>a phosphorescent platinum (II) or palladium(II) porphyrin</u>

Col. 12, line 50: ~~tonable dye embedded in a polymer, in which the dye in~~ should read <u>tonable dye embedded in a polymer, in which the dye is</u>

Col. 12, line 51: ~~a phosphorent platinum (II) or palladium(II) porphyrin~~ should read <u>a phosphorescent platinum (II) or palladium(II) porphyrin</u>

Signed and Sealed this  
Nineteenth Day of August, 2014

Michelle K. Lee  
*Deputy Director of the United States Patent and Trademark Office*